United States Patent [19]

Comparetto

[11] 4,270,901
[45] Jun. 2, 1981

[54] DENTAL ARTICULATOR

[76] Inventor: John E. Comparetto, Star Rte., Box 66, Machipongo, Va.

[21] Appl. No.: 932,110

[22] Filed: Aug. 9, 1978

[51] Int. Cl.³ ............................................. A61C 19/00
[52] U.S. Cl. ..................................................... 433/54
[58] Field of Search .............. 32/32; 33/23 C; 433/55, 433/54

[56] References Cited

U.S. PATENT DOCUMENTS

| | | | |
|---|---|---|---|
| 1,904,623 | 4/1933 | Malcolm et al. | 32/23 C |
| 2,025,344 | 12/1935 | Fischer | 433/34 |
| 2,678,495 | 5/1954 | Fine | 32/32 |
| 2,754,589 | 7/1956 | Highkin | 32/32 |
| 3,321,832 | 5/1967 | Weisberg | 32/32 |
| 3,452,439 | 7/1969 | Lee | 32/32 |

*Primary Examiner*—Robert Peshock
*Attorney, Agent, or Firm*—James C. Wray

[57] ABSTRACT

A dental articulator which provides a three-dimensional solid cam temporomandibular joint model of a human jaw movement by carving an internal cavity into said three-dimensional solid cam model by a cutting stylis.

6 Claims, 6 Drawing Figures

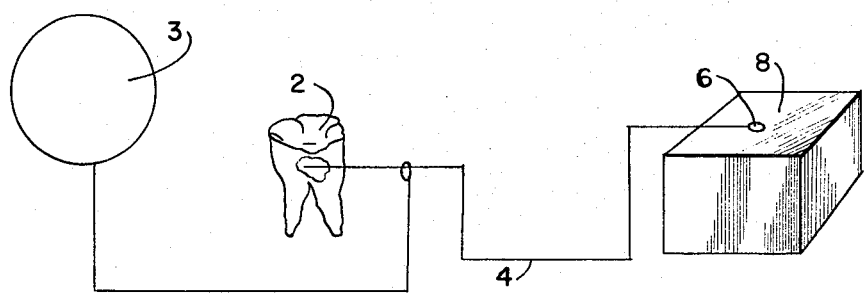
FIG. 1
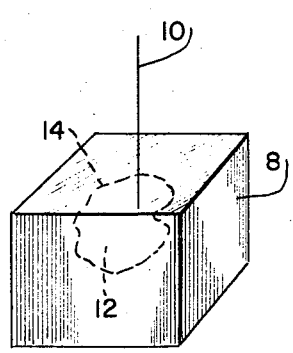
FIG. 2
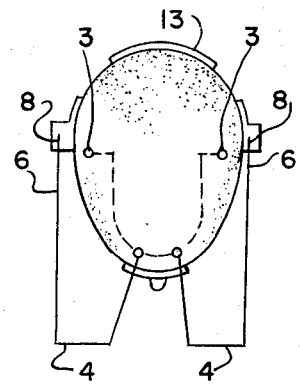
FIG. 3
FIG. 4
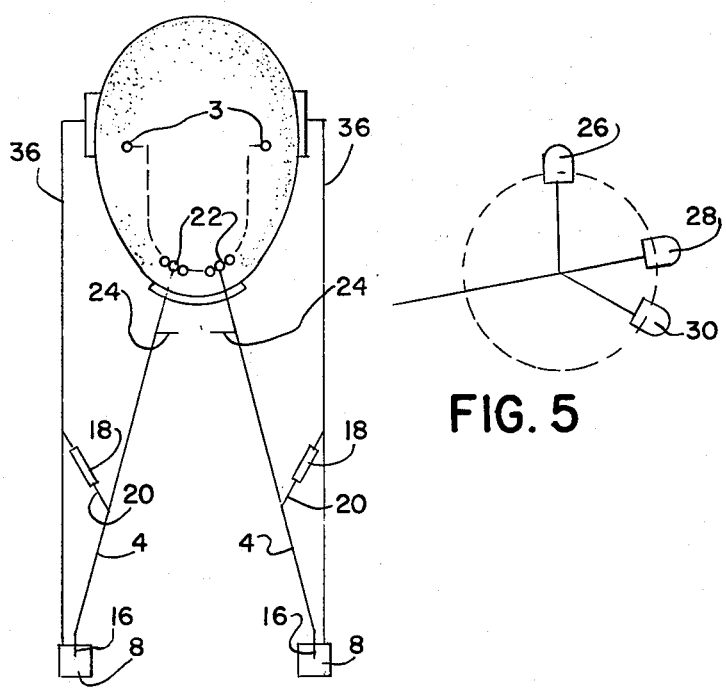
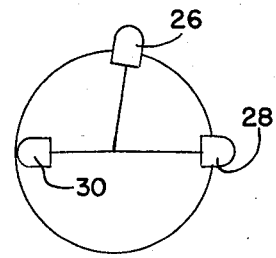
FIG. 5    FIG. 5A

DENTAL ARTICULATOR

BACKGROUND OF THE INVENTION

The present invention is an accurate and precise method for duplicating the action of the temporomandibular joint (TMJ).

OBJECTS OF THE INVENTION

An object of the invention is to provide a three-dimensional solid cam temporomandibular joint excursion model for recording human jaw movements.

Other objects of the invention are to provide means for using the three-dimensional solid cam model wherein human jaw movements are recorded, a mandibular frame member connected to the three-dimensional solid cam model, guide means mounted on a mandibular frame for directing means for using the three-dimensional solid cam and holding means for positioning a human jaw.

Another object of the invention is to provide means for using the three-dimensional solid cam model comprising forming means for shaping the three-dimensional cam model.

Another object of the invention is to provide forming means comprising a cutting stylus.

Another object of the invention is to provide a cutting stylus comprising a hot point, a blade, a laser, or a syringe needle whereby the stylus carves a replica of the movements of a human jaw.

Another object of the invention is to provide following means comprising a wheeled stylus which duplicates the movements of a human jaw.

Another object of the invention is to provide guide means comprising a spring tensioned arm for providing a smooth simulation of human jaw movements.

Another object of the invention is to provide holding means comprising frontal and occipital clamps.

Another object of the invention is to provide a three-dimensional solid cam model comprising an internal cavity which approximates the movements of a human jaw.

Another object of the invention is to provide a three-dimensional solid cam model comprising an external replica of human jaw movements.

Another object of the invention is to provide a method of simulating human jaw movement comprising the steps of using a three dimensional solid cam model of temporomandibular joint movement.

Another object of the invention is to provide tracing comprising following the three-dimensional cam model wherein the three-dimensional cam model is an external replica of human jaw movement.

Another object of the invention is to provide a method of forming comprising carving an internal cavity into the three-dimensional solid cam model by a cutting stylus.

Another object of the invention is to provide a method of following comprising traveling over the external replica of human jaw movement with a wheeled stylus.

BRIEF DESCRIPTION OF THE DRAWINGS

FIG. 1—shows a side view of the dental articulator indicating the connection points FIG. 2—shows the block into which the tenparomantebular movement is carved out.

FIG. 3—shows the top view of the first embodiment for cutting temparomandibular joint carvings.

FIG. 4—shows the top view of a second embodiment for cutting temparomandibular joint carvings.

FIGS. 5 and 5A show discretely demarcated indicators of triplane movement.

DETAILED DESCRIPTION OF THE DRAWINGS

In FIG. 1, circle 3 represents a temporomandibular joint TMJ. A tooth 2, in this illustration represents a mandibular cuspid. A rigid member 4 with stylus 6 is mounted within block 8. Block 8 is made of a material with the quality of being able to be melted, evaporated, scraped or washed away by stylus 6.

Some examples of block 8 material might be wax, rigid foam, styrofoam, balsam, duralay, etc.

Stylus 6 may be a hot point, a blade, a laser, or a syringe needle capable of being fed first an acid for etching and then a base for neutralizing so that incremental cutting or dissolving can be accomplished.

Block 8 is penetrated by stylus 6 while a patient's teeth are in centric relation. Section 4 on each side is affixed to a satisfactory tooth or teeth 2 that will allow no shifting.

In edentulous patients member 4 will be affixed directly to the anesthetized mandible.

From the centric position of stylus 6 the patient is slowly taken through all jaw excursions while the point 6 cuts the material 8 in a manner afforded by the examples above.

A pin marker 10, FIG. 2, is made through block 8 to the centric position of stylus 6 for reestablishing the dental models on the articulator.

The carved-out area of block 8 corresponds to the exact amount of movement or "displacement" of the corresponding temporomandibular joint.

A positive model 14 of carving 12 of block 8 may be poured with pin 10, connected.

The model may be isolated at this point from block 8 and used two ways.

The positive carving 14 can be attached to the articulator and a small wheeled stylus may be made to travel over the carving 14 corresponding to the patient's temporomandibular joint movement.

The carving 12 itself within the original block 8, or a subsequent permanent poured block $8^2$ may be made over carving 14 allowing carving 14 to be removed. Carving cavity 12 can be used with a small caster type "cold" stylus that can move within the cavity 12, corresponding to all the patient's temporomandibular joint movements made by the block-carving "hot" stylus.

A number of methods can be used for setting up the making of the patient's temporomandibular joint carvings. FIGS. 3 and 4 represent two methods.

Another method of forming the hollowed out cam block employs a round dental burr and vacuum line to draw off burrings. In all cases means are provided to remove the carved out material. For example, some gassifies and permeates the mold. In other cases, drains or vacuum removes the fluid or fluent material.

Guide arm 36 would keep cold stylus 16 against the carving 12 as needed especially in non-patient helped guidance. Guide arm 18 would contain a small spring 20 for mild tension.

It might be beneficial to form carving 12 unilaterally or one at the time or it may prove advantageous to form them simultaneously with movements of each stylus 6 effecting the carving 12 of each other.

Mounting of the dental models should be done to correspond with mandibular frame 4 connections to teeth or mandible.

With carving 12 formed, the patient's dental models could be mounted by the dentist and patient in the following manner. Tooth attachments capping like devices for affixing members 4 could have a duplicate attachment at point 24 wherein the mandibular model would be mounted upside down to correspond to the "real" image of temporomandibular joint's created in carving 12 diagonally. The turning over of the models would be unnecessary if members 4 were criss-crossed.

At this point in the case where there is no preexisting malocclusion, the patient and dentist will bring the models into centric mounting position. After this mounting is accomplished, excursive movements can be reduplicated with the patient's and carving 12 guidance.

In cases of malocclusion, alternate equilibrations of patient and model in disjointed separate grindings may be a worthy methodology.

Stylus 6 would most effectively be angled into block 8 for the fabrication of carving cavity 12 in a way that corresponds to the direction of the condyle into the temporomandibular joint. The "cuttings" might consist of a series of tracts or various excursions, i.e., the multiplaned movements of the temporomandibular joint would probably conform to three basic planes and would also record normal side shift as well as idiosyncratic shiftings. In cases where e.g. lateral movement groovings of right and left differ tremendously while radiographs do not confirm or indicate an osseous reason, ligamentous and muscular imbalance might be more easily pinpointed. These imbalances might then be remedied prior to attempting final equilibration.

Materials for block 8 should ideally have the qualities aforementioned but additionally the substance left would ideally be hard enough to withstand movements of "cold" stylus during equilibrations. If only softer materials such as waxes can be found, then making a block 8a by positive carving 14 and negative carving cavity 12 models will be necessary unless shellacing or other hardening sprays can be made to accomplish same.

A block 8a articulator would be set up to maintain patient to head rest, patient to model, and patient to block 8a carving cavity 12 distances.

In order to measure more completely the tri-planar motion, a single stylus point may not be sufficient. This instance can be visualized by protrusive jaw movement where stylus movement is in the sagittal place only with no or very little movement in the frontal or transverse planes.

While a small sphere as the "hot point" has dimension in all planes, it might be more useful to have discretely demarcated indicators of triplane movement, blades 26, 28, 30 depicting frontal, sagittal, and transverse planes respectively.

The curved line represents pure sagittal plane movement of a protrusion of mandible blades 1 and 3 would make corresponding fixed frontal and transverse plane references.

This adjunct may or may not prove necessary.

What is claimed is:

1. A dental articulator apparatus for forming a three-dimensional solid cam temporomandibular joint excursion model for reproducing human jaw movements within an internal solid cavity cam model, further comprising means for making the three-dimensional solid cam model wherein human jaw movements are recorded, comprising following means for following movements of the human jaw and duplicating movements of the human jaw with said internal cavity, a mandibular frame member connected to the three-dimensional solid cam model and to the means for making the three-dimensional solid cam model for recording human jaw movement within said internal cavity solid cam model, guide means mounted on a mandibular frame for directing means for making the three-dimensional solid cam for recording human jaw movements within said internal cavity solid cam model, holding means for positioning a human jaw connected to the mandibular frame for permitting the means for making the three-dimensional solid cam model to record human jaw movements and forming means for forming a three-dimensional solid cam model external replica of human jaw movements within said internal cavity solid cam model.

2. The apparatus of claim 1 wherein the cutting stylus comprises a hot point, a blade, a burr, a laser, or a syringe needle whereby the stylus carves a replica of the movements of a human jaw within the three-dimensional solid cam model.

3. The apparatus of claim 1 wherein the guide means comprises a spring tensioned arm for providing a smooth simulation of human jaw movements.

4. The apparatus of claim 1 wherein holding means comprises frontal and occipital clamps.

5. The apparatus of claim 1 wherein the three-dimensional solid cam model is made from materials such as styrofoam, balsam, or wax, or dental stone.

6. A method of making a block for simulating human jaw movement comprising the steps of forming and then using a three-dimensional solid cam model of temporomandibular joint movement inserting a cutting stylus in a block connecting the cutting stylus to a human jaw to move with movement of the human jaw, conducting the jaw through excursions and thereby comprising carving an internal cavity in the block with the cutting stylus; pouring a substance into the internal cavity; forming an external replica of the internal cavity.

* * * * *